US010792157B2

(12) United States Patent
Zhang

(10) Patent No.: US 10,792,157 B2
(45) Date of Patent: Oct. 6, 2020

(54) FUSED FEMORAL STEM SYSTEM

(71) Applicant: Beijing AK Medical Co., Ltd, Beijing (CN)

(72) Inventor: Weiping Zhang, Beijing (CN)

(73) Assignee: BEIJING AK MEDICAL CO., LTD, Beijing (CN)

( * ) Notice: Subject to any disclaimer, the term of this patent is extended or adjusted under 35 U.S.C. 154(b) by 0 days.

(21) Appl. No.: 15/966,053

(22) Filed: Apr. 30, 2018

(65) Prior Publication Data

US 2019/0105162 A1 Apr. 11, 2019

(30) Foreign Application Priority Data

Oct. 9, 2017 (CN) .......................... 2017 1 0928930

(51) Int. Cl.
*A61F 2/32* (2006.01)
*A61F 2/36* (2006.01)
(Continued)

(52) U.S. Cl.
CPC .......... *A61F 2/3609* (2013.01); *A61F 2/3094* (2013.01); *A61F 2/30734* (2013.01);
(Continued)

(58) Field of Classification Search
CPC .. A61F 2/32; A61F 2/34; A61F 2/4609; A61F 2/36; A61F 2/30; A61F 2/3609;
(Continued)

(56) References Cited

U.S. PATENT DOCUMENTS

| | | | |
|---|---|---|---|
| 4,488,319 A | 12/1984 | Von Recum |
| 5,571,203 A | 11/1996 | Masini |

(Continued)

FOREIGN PATENT DOCUMENTS

| | | |
|---|---|---|
| DE | 2854334 A1 | 6/1980 |
| EP | 0308081 A1 | 3/1989 |

OTHER PUBLICATIONS

European Search Report for EP18167087; dated Nov. 6, 2018.

*Primary Examiner* — Ann Schillinger
(74) *Attorney, Agent, or Firm* — AKC Patents, LLC; Aliki Collins

(57) ABSTRACT

The present invention provides a fused femoral stem system, including a curved short handle, a fixing mechanism and a femoral head prosthesis, one end of the curved short handle is provided with a conical connector, the conical connector is cooperatively connected with a conical connecting hole of the femoral head prosthesis, the other end of the curved short handle is inserted from the osteotomy surface of the femoral neck and stretches to the position of a medullary cavity below a small trochanter, and the curved short handle is connected and fixed with a large trochanter through the fixing mechanism. The present invention has the beneficial effects that, after the growing-in osseointegration with the sclerotin surrounding the proximal bone bed of the host after the surgery of the whole system, the mechanical influence on the retained femoral neck and the sclerotin in the vicinity of the large and small trochanters is substantially similar to the biomechanical state prior to the surgery.

9 Claims, 8 Drawing Sheets

(51) Int. Cl.
*A61B 17/74* (2006.01)
*A61F 2/30* (2006.01)
*A61B 17/86* (2006.01)

(52) U.S. Cl.
CPC ............ *A61F 2/30965* (2013.01); *A61F 2/32* (2013.01); *A61F 2/3662* (2013.01); *A61F 2/3672* (2013.01); *A61B 17/74* (2013.01); *A61B 17/742* (2013.01); *A61B 17/8685* (2013.01); *A61F 2/30* (2013.01); *A61F 2/36* (2013.01); *A61F 2002/30011* (2013.01); *A61F 2002/3085* (2013.01); *A61F 2002/30113* (2013.01); *A61F 2002/30125* (2013.01); *A61F 2002/30138* (2013.01); *A61F 2002/30153* (2013.01); *A61F 2002/30159* (2013.01); *A61F 2002/30726* (2013.01); *A61F 2002/30738* (2013.01); *A61F 2002/30948* (2013.01); *A61F 2002/30957* (2013.01); *A61F 2002/30968* (2013.01); *A61F 2002/30985* (2013.01); *A61F 2002/3654* (2013.01); *A61F 2310/00011* (2013.01)

(58) Field of Classification Search
CPC ............ A61F 2/3859; A61F 2002/3611; A61F 2/3662; A61F 2002/30649; A61F 2002/30973; A61F 2002/3822
See application file for complete search history.

(56) References Cited

U.S. PATENT DOCUMENTS

2008/0183171 A1* 7/2008 Elghazaly .......... A61B 17/7241 606/64
2012/0010723 A1* 1/2012 Walter .................. A61F 2/4607 623/23.18
2014/0172115 A1* 6/2014 Porter ....................... A61F 2/32 623/23.15

* cited by examiner

FUSED FEMORAL STEM SYSTEM

CROSS REFERENCE TO RELATED CO-PENDING APPLICATIONS

This application claims the benefit of Chinese National patent application Serial No. 201710928930.7 filed Oct. 9, 2017 and entitled “FUSED FEMORAL STEM SYSTEM”, the contents of which are expressly incorporated herein by reference.

FIELD OF THE INVENTION

The present invention relates to the field of orthopedic implantation, and more specifically relates to a fused femoral stem system for primary replacement, which can maximally retain femoral necks.

BACKGROUND OF THE INVENTION

Avascular necrosis of the femoral head is a common progressive disease, and when it is advanced to the later period, it usually requires an artificial hip replacement surgery, that is, the necrotic femoral head is firstly cut off, and then a femoral stem carrying or provided with an artificial femoral head is implanted in the femoral medullary cavity to replace the truncated physiological femoral head. At present, the design of femoral stems of various companies requires osteotomy from the large trochanter to the small trochanter in a hip joint thighbone replacement surgery in most cases, the necrotic femoral head is cut off with the femoral necks, but in most cases, the sclerotin of the femoral necks is basically healthy and intact, sometimes even the lower hemisphere of the femoral head is basically intact, and it is a pity that these intact parts are completely cut off in the femoral osteotomy; in order to keep more femoral necks, a few brands of femoral stems adopt a short handle design to facilitate direct insertion into the femoral medullary cavity, but due to excessive complex mechanical environment applied to the femoral necks in the normal daily life of human body such as tension, pulling out, twisting and the like, the stability of the femoral stem is reduced until the femoral stem becomes loose and ineffective in the future.

SUMMARY OF THE INVENTION

The present invention overcomes the deficiencies in the prior art and provides a fused femoral stem system. The fused femoral stem system is of a short handle design to retain as many femoral necks as possible, and at the same time, the mechanical influence is substantially similar to the biomechanical state prior to the surgery so as to ensure the stability of the femoral stem system.

The objective of the present invention is achieved by the following technical solutions.

A fused femoral stem system includes a curved short handle, a fixing mechanism and a femoral head prosthesis, the fixing mechanism includes a lag screw and a fused screw sleeve, the fused screw sleeve penetrates a large trochanter, the lag screw is connected and locked with a connecting mechanism by penetrating through the fused screw sleeve so as to counteract a downward bending moment generated when the femoral head bears the weight load after the surgery, one end of the curved short handle is provided with a conical connector, the conical connector is cooperatively connected with a conical connecting hole of the femoral head prosthesis, and the other end of the curved short handle is inserted from the osteotomy surface of the femoral neck and stretches to the position of a medullary cavity below a small trochanter, and the curved short handle is fixed with the large trochanter through the fixing mechanism.

Further, a metal short handle satisfying the morphological characteristics of the curved surface of the inner wall of a cortical bone on the lower half part of the retained physiological femoral head is arranged on the lower surface of the handle body of the curved short handle close to the conical connector.

Further, the cross section of the curved short handle is rectangular, circular, elliptical, drop-shaped or polygonal.

Further, bone fusion layers are arranged at contact positions of the curved short handle with the medullary cavity and the large trochanter.

Further, the bone fusion layer is a rough coating obtained by plasma high-temperature spraying or a porous layer formed by sintering metal powder or metal particles or a porous metal layer directly generated by 3D printing.

Further, a connecting mechanism is arranged on a side of the curved short handle facing to the large trochanter.

Further, the fused screw sleeve is a hollow tubular body that penetrates from the outside of the large trochanter, the outer surface thereof is of a metal porous structure, and the inner surface thereof is of a solid metal sleeve structure.

Further, the fused screw sleeve is designed with an enlarged annular structure at the outside of the bone cortex of the large trochanter.

Further, the annular structure is provided with a porous structure on the side close to the surface of the cortical bone of the large trochanter.

Further, the lower surface of the handle body of the curved short handle close to the conical connector is of a metal porous structure.

The beneficial effects of the present invention are as follows:

After the growing-in osseointegration with the sclerotin surrounding the host after the surgery of the whole system, the mechanical influence on the retained femoral neck and the sclerotin in the vicinity of the large and small trochanters is substantially similar to the biomechanical state prior to the surgery;

the short handle design has no damage to the medullary cavity of the femoral shaft below the small trochanter, and the wound is little; and more sclerotin is provided for subsequent possible joint revision.

REFERENCE SIGNS

Figure 1:
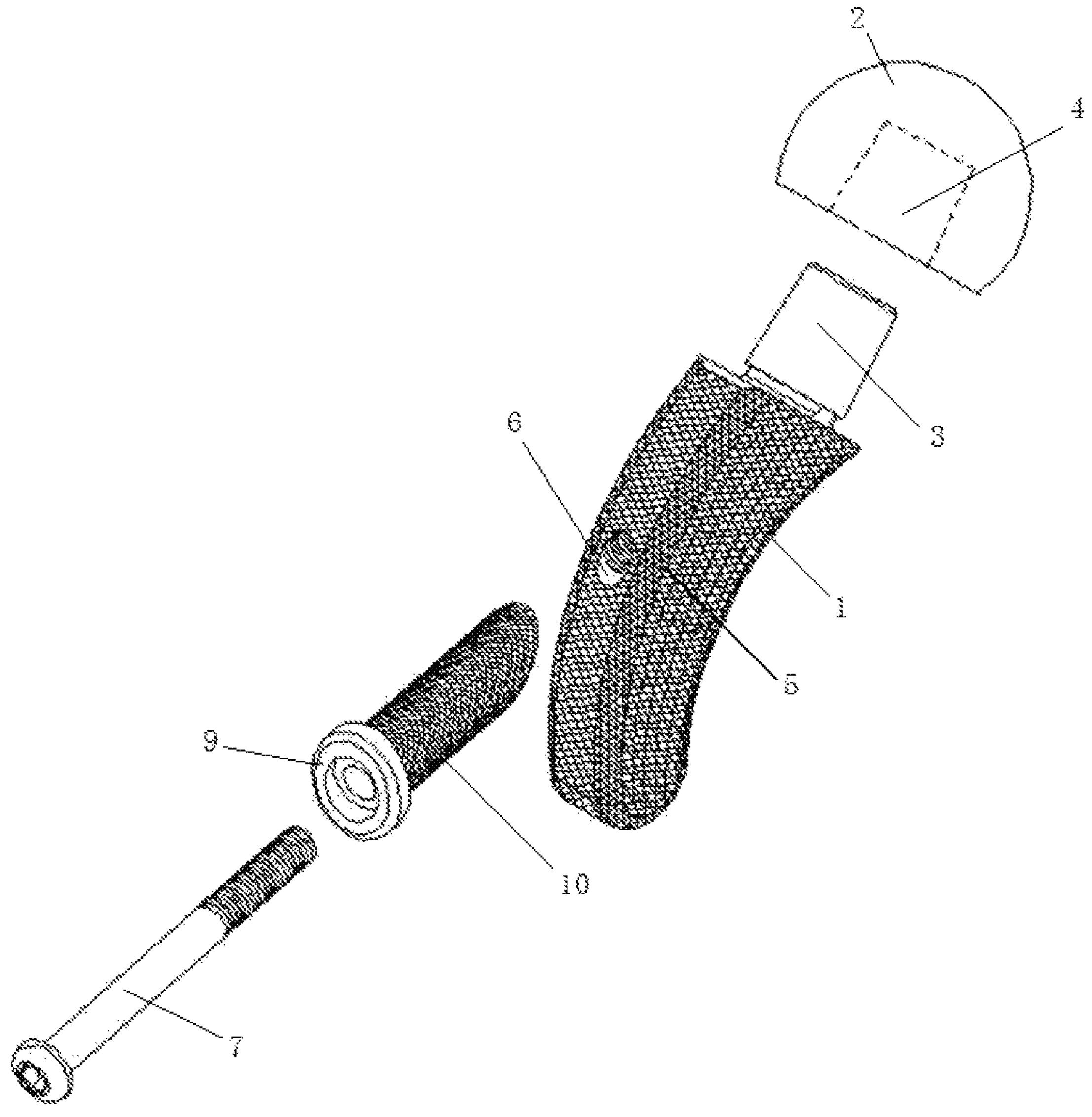
FIG. 1 is a structure diagram of a fused femoral stem system.
Figure 2:
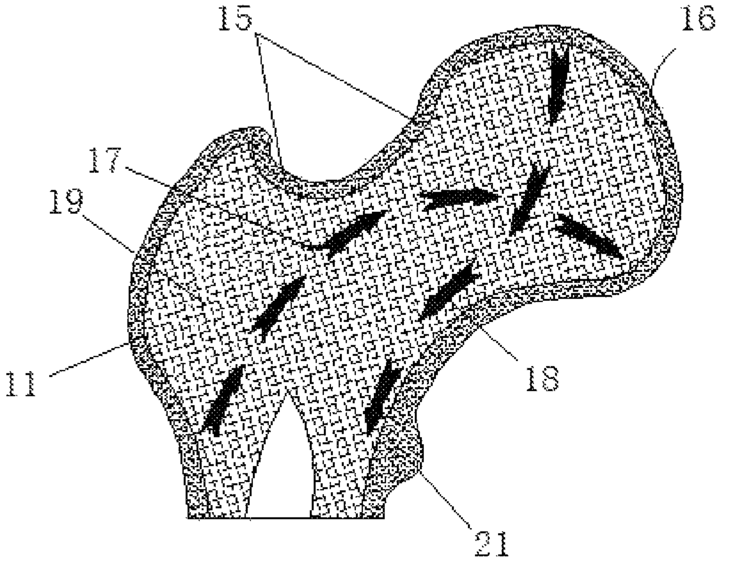
FIG. 2 is a structure diagram of a physiological femoral head of a human body.
Figure 3:
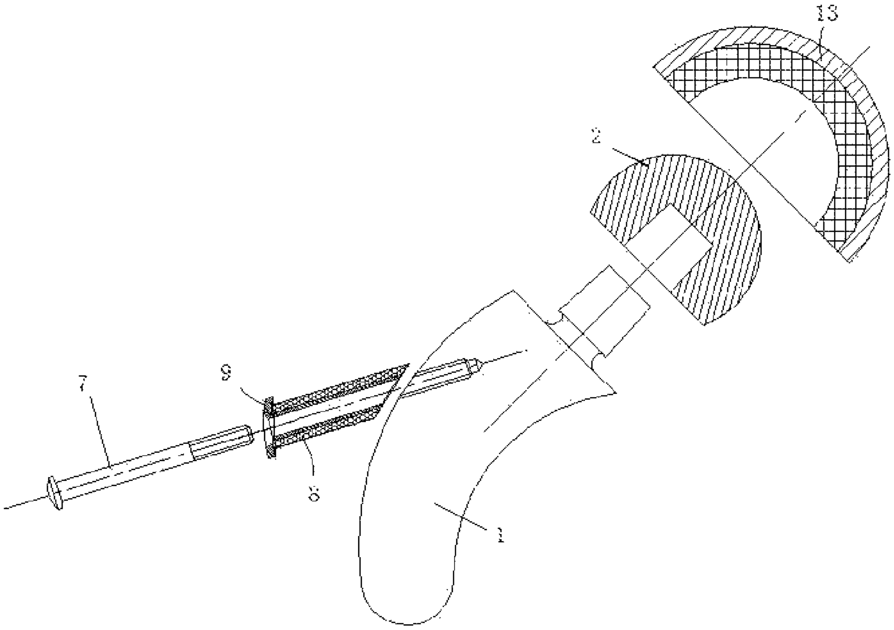
FIG. 3 is a schematic diagram of a combination process of a fused femoral stem system.

1. curved short handle; 2. femoral head prosthesis; 3. conical connector; 4. conical connecting hole; 5. bone fusion layer; 6. connecting structure; 7 lag screw; 8. fused screw sleeve; 9. annular structure; 10. porous structure; 11. large trochanter; 12. medullary cavity; 13. outline of damaged part of cut-off physiological femoral head; 14. solid metal sleeve; 15. femoral neck; 16. femoral head; 17. tension line; 18. pressure line; 19. cancellous bone; 20. cortical bone; 21. small trochanter; 22. circular truncated cone; 23. platform; 24. acetabular cup prosthesis.

DETAILED DESCRIPTION OF THE INVENTION

The technical solutions of the present invention will be further described below through specific embodiments.

As shown in FIG. 1, FIG. 3, FIG. 4, FIG. 5 and FIG. 6, a fused femoral stem system includes a curved short handle 1, a fixing mechanism and a femoral head prosthesis 2, one end of the curved short handle 1 is provided with a conical connector 3, the femoral head prosthesis 2 is connected via a conical connecting hole 4 of the femoral head prosthesis 2, the other end of the curved short handle 1 is inserted from the osteotomy surface of a femoral neck 15 and stretches to the position of a medullary cavity 12 below a small trochanter 21, the curved short handle 1 is fixed with a large trochanter 11 via the fixing mechanism; and in actual operation, it is not necessary to cut off the lower hemisphere of the bone-healthy femoral head or the femoral neck 15 to provide more sclerotin for the future joint revision. The diameter of the femoral head prosthesis 2 is slightly larger than an outline 13 of a damaged part of a cut-off physiological femoral head so as to facilitate the matching of a modified acetabular fossa bone bed.

The curved short handle is a metal short handle satisfying the anatomical bending features of the femoral neck 15, which generates no damage and little wound to the medullary cavity 12 of a femoral shaft below a small trochanter 21.

The cross section of the curved short handle 1 is rectangular, circular, elliptical, drop-shaped or polygonal; bone fusion layers 5 are arranged at contact positions of the outer surface of the curved short handle 1 with the medullary cavity 12 and the large trochanter 11; and the bone fusion layer 5 is a rough coating obtained by plasma high-temperature spraying or a porous layer formed by sintering metal powder or metal particles or a porous metal layer directly generated by 3D printing.

The fixing mechanism includes a lag screw 7 and a fused screw sleeve 8, and the lag screw 7 is connected and locked with a connecting mechanism 6 by penetrating through the fused screw sleeve 8 from the outside of the large trochanter 11; and the connecting mechanism 6 is connected and locked with the external cortex of the large trochanter 11 through the lag screw 7 and the fused screw sleeve 8 so as to counteract a downward bending moment generated when the femoral head bears the weight load after the surgery.

The fused screw sleeve 8 is a hollow tubular body that penetrates from the outside of the large trochanter 11, the outer surface thereof is of a metal porous structure 10, and the inner surface thereof is of a solid metal sleeve structure 14; the metal porous structure 10 can produce growing-in osseointegration with the sclerotin coated surrounding this structure after the surgery, the inner surface of the center through hole of the fused screw sleeve 8 is designed into a solid metal sleeve structure 14 to provide sufficient compression resistance and bending resistance, and the metal porous structure 10 on the outer surface of the fused screw sleeve 8 and the solid metal sleeve structure 14 therein are of an integrated structure.

The fused screw sleeve 8 is designed with an enlarged annular structure 9 at the outside the bone cortex of the large trochanter 11.

The annular structure 9 is provided with a porous structure 10 on the side close to the surface of the cortical bone 20 of the large trochanter 11.

The lag screw 7 is connected and locked with the connecting mechanism 6 by penetrating through the fused screw sleeve 8 from the outside of the large trochanter 11, during this locking process, the screw cap of the lag screw 7 presses the annular structure 9 of the fused screw sleeve 8 on the outer surface of the bone cortex of the large trochanter, and the porous structure 10 on the annular structure 9 produces growing-in osseointegration with the bone cortex on the surface of the large trochanter after the surgery.

Figure 4:
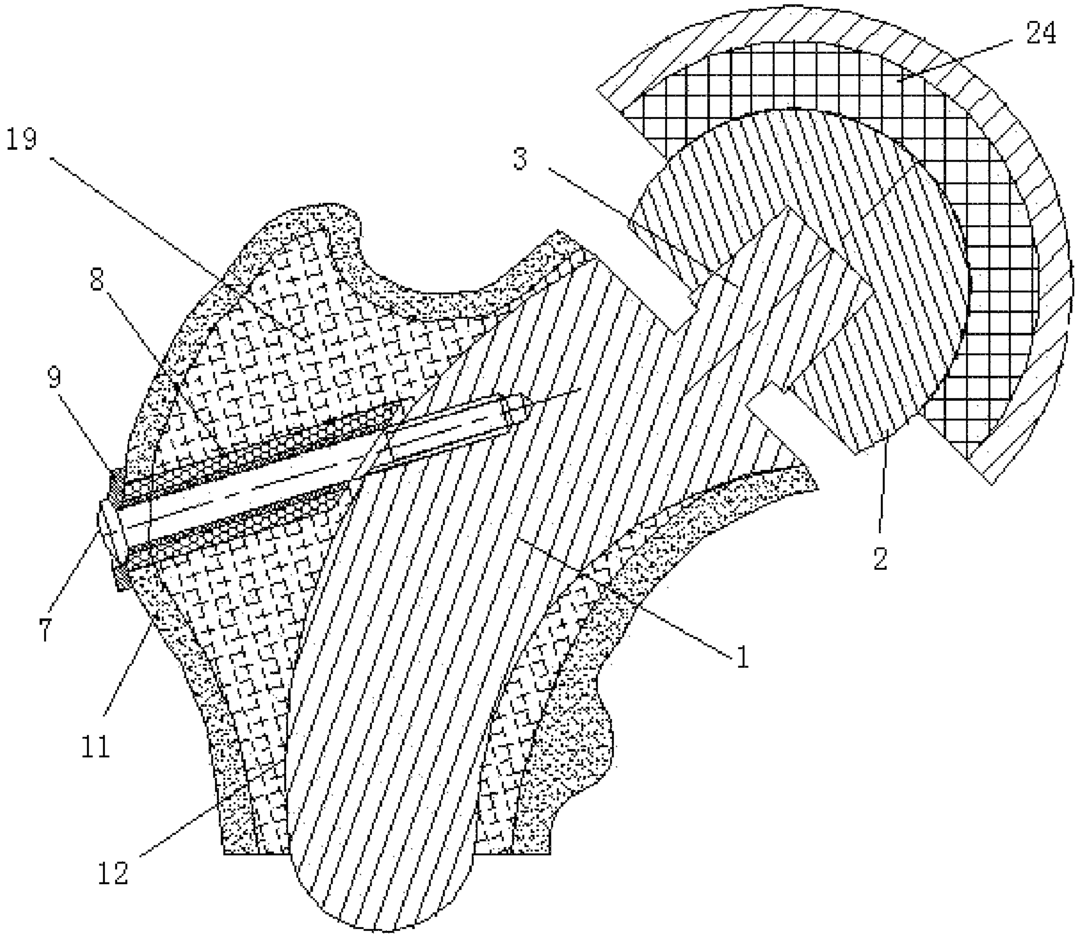
FIG. 4 is a schematic diagram of a combination process of a fused femoral stem system with the femoral head being completely cut off.

As shown in FIG. 4, after the femoral head is completely cut off, a metal short handle satisfying the morphological characteristics of the curved surface of the inner wall of the cortical bone 20 on the lower half part of the retained physiological femoral head is arranged on the lower surface of the handle body of the curved short handle 1 close to the conical connector.

As shown in FIG. 7a, FIG. 7b, FIG. 8a and FIG. 8b, in order to maximally retain the femoral neck, the metal short handle satisfying the morphological characteristics of the curved surface of the inner wall of the cortical bone 20 on the lower half part of the retained physiological femoral head is arranged on the lower surface of the handle body of the curved short handle 1 close to the conical connector, the curved short handle can be designed into a curved short handle provided with a circular truncated cone 22 and can also be designed into a curved short handle provided with a platform 23 to adapt to different implantation demands.

Figure 5:
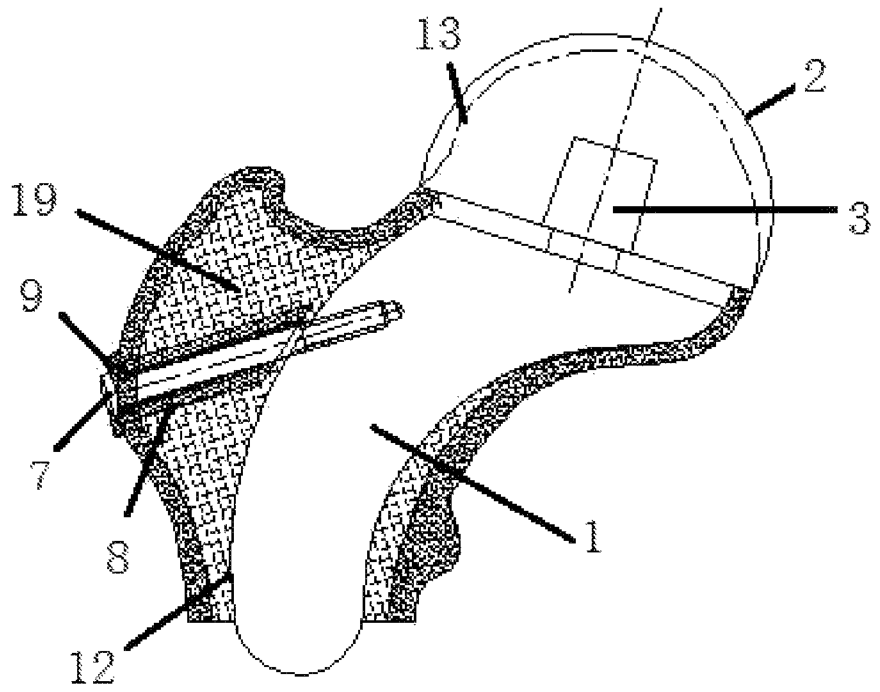
FIG. 5 is a schematic diagram of a use state of a fused femoral stem system when a lower half part of a physiological femoral head is retained.
Figure 6:
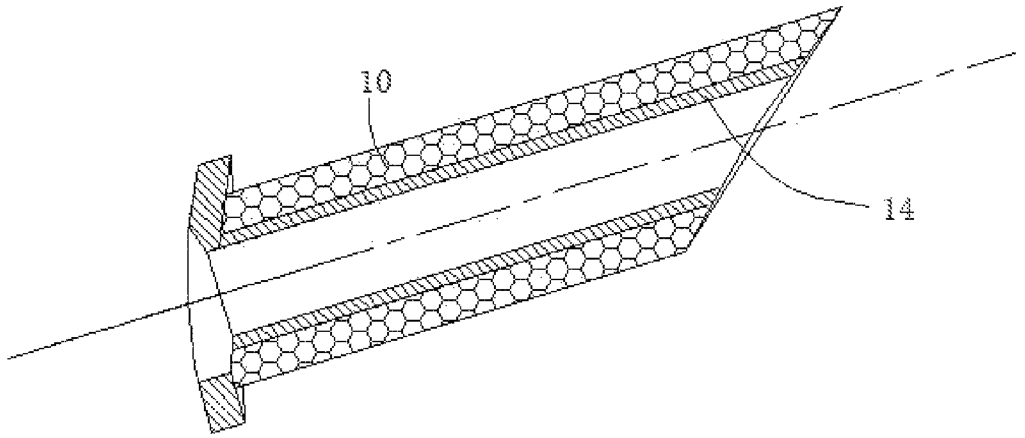
FIG. 6 is a structure diagram of a fused screw sleeve.
Figure 7A:
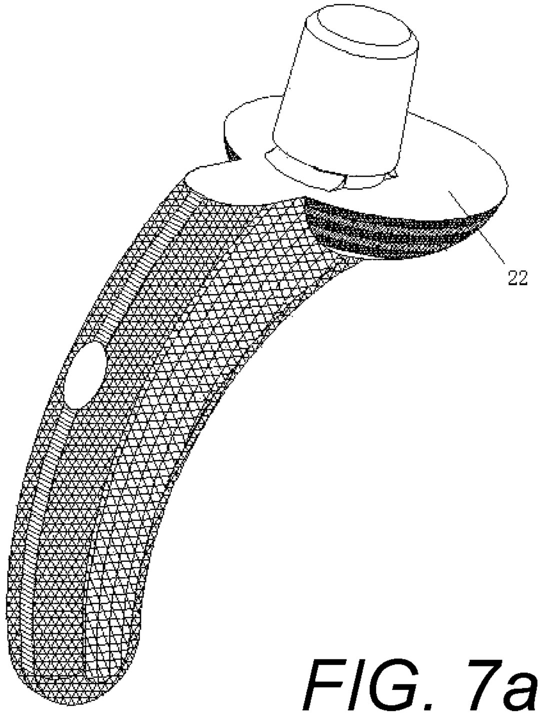
FIG. 7*a* is a schematic diagram of a curved short handle having a lower edge of a handle body satisfying the morphological characteristics of a curved surface of an inner wall of a cortical bone on the lower half part of the physiological femoral head and provided with a circular truncated cone.
Figure 7B:
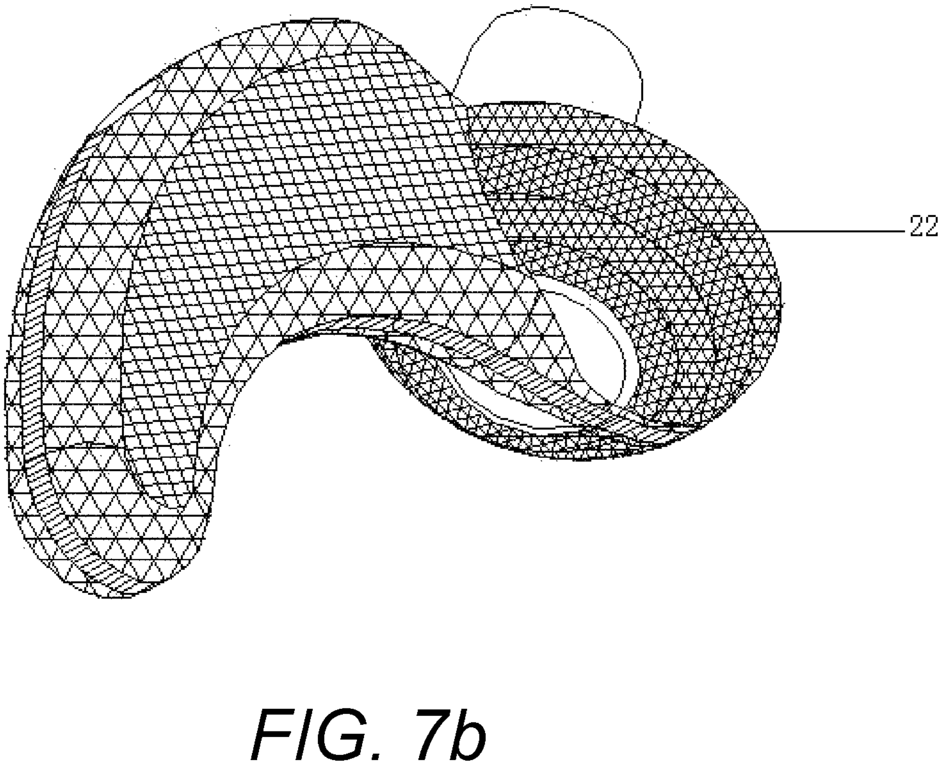
FIG. 7b is an upward view of a curved short handle having a lower edge of a handle body satisfying the morphological characteristics of a curved surface of an inner wall of a cortical bone on the lower half part of the physiological femoral head and provided with a circular truncated cone.
Figure 8A:
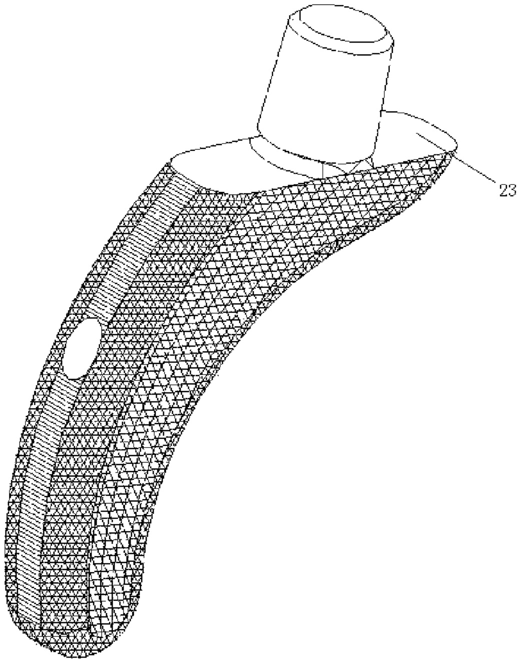
FIG. 8a is a schematic diagram of a curved short handle having a lower edge of a handle body satisfying the morphological characteristics of a curved surface of an inner wall of a cortical bone on the lower half part of the physiological femoral head and provided with a platform.
Figure 8B:
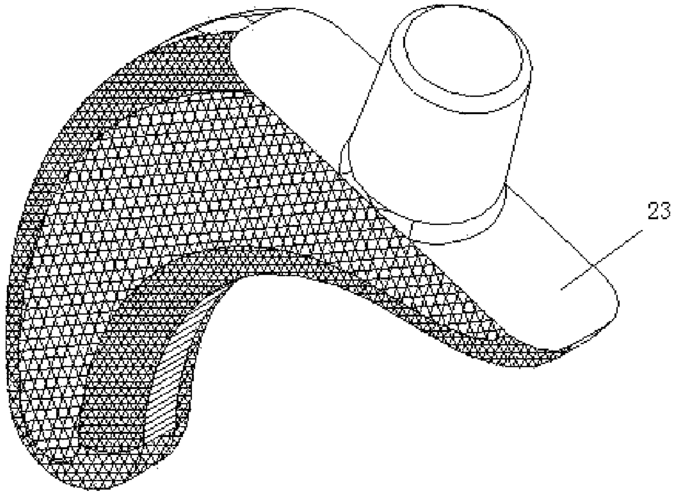
FIG. 8b is a top view of a curved short handle having a lower edge of a handle body satisfying the morphological characteristics of a curved surface of an inner wall of a cortical bone on the lower half part of the physiological femoral head and provided with a platform.
Figure 9:
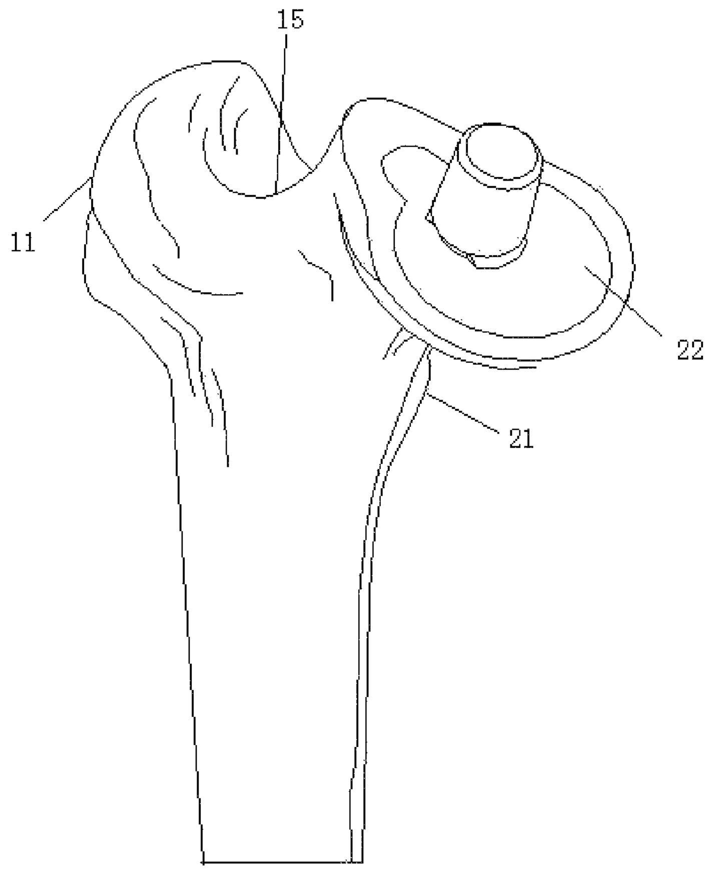
FIG. 9 is an installation diagram of a curved short handle provided with a circular truncated cone.
Figure 10:
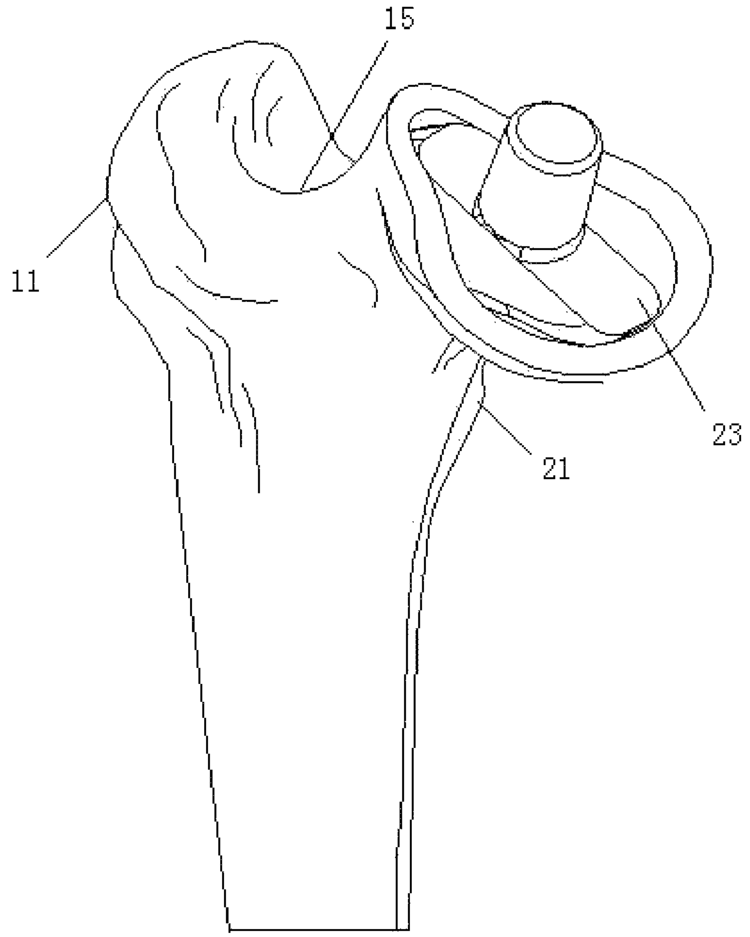
FIG. 10 is an installation diagram of a curved short handle provided with a platform.

As shown in FIG. 5, FIG. 9 and FIG. 10, the fused femoral stem system will form a stable implanted mechanical system after the surgical implantation, the gravity load transferred by the femoral head prosthesis 2 is transferred to the sclerotin of the lower half part of the retained physiological femoral head by the surface satisfying the morphological characteristics of the curved surface of the inner wall of the cortical bone 20 on the lower half part of the retained physiological femoral head arranged on the lower part of the handle body of the curved short handle 1 close to the conical connector 3, and the function of the sclerotin of the lower half part of the retained physiological femoral head in the biomechanical system before the surgery is to bear the support to the upper half part of the femoral head; the lower surface of the handle body of the curved short handle 1 close to the conical connector 3 is of a metal porous structure, and the metal porous structure can form growing-in osseointegration with the sclerotin of the lower half part of the retained physiological femoral head in a rehabilitation process after the surgery to obtain a long-term stable effect.

In the rehabilitation process, the growing-in osseointegration is generated with the sclerotin on the upper layer of the femoral neck 15 coated on its surrounding and mainly bears the tensile stress load, and the function of the sclerotin on the upper side of this part of physiological femoral neck 15 in the biomechanical system before the surgery is to bear the tensile stress transferred by the femoral head; and the lag screw 7 pulls the curved short handle 1 after penetrating through the fused screw sleeve 8 from the outside of the large trochanter 11 so as to counteract the downward bending moment generated when the femoral head bears the weight load after the surgery, the porous metal structure 10 on the outer surface of the fused screw sleeve 8 generates the growing-in osseointegration with the sclerotin coated surrounding the porous metal structure, and this integration effect transfers the downward bending moment of the femoral stem 1 under the pressure of the femoral head into the tensile stress of the sclerotin on the upper side of the femoral neck 15 and relieves the pressure of the lag screw 7 on the outside of the large trochanter 11.

The manufacturing process of the fused femoral stem system of the present invention is as follows:

First, obtaining a curved short handle blank by using a forging or casting process, machining the blank into the size of a finished product by using a conventional machining cutting process, reserving a spray coating thickness of the bone fusion layer, and performing plasma high temperature spray coating on the part requiring coating to obtain a rough coating;

Next, obtaining the curved short handle blank by using the forging or casting process, machining the blank into the size of the finished product by using the conventional machining cutting process, reserving a sintering coating thickness of the bone fusion layer, and sintering the part requiring coating by using metal power or metal particles to obtain a metal particle sintered porous layer;

Next, designing a three-dimensional model of the curved short handle in a computer, designing the necessary location on the surface of the curved short handle into a three-dimensional model of the porous metal structure, performing CT or MIR scanning on the lower half part of the retained physiological femoral head, performing reverse modeling on the scanning data to obtain the morphological characteristics of the curved surface of the inner wall of the cortical bone 20 on the lower half part of the retained physiological femoral head, designing the surface morphology of the lower part of the handle body of the curved short handle close to the conical connector according to the morphological characteristics of the curved surface of the inner wall of the cortical bone 20 on the lower half part of the retained physiological femoral head so as to form good union between the outer surface of the lower part of the handle body close to the conical connector and the curved surface of the inner wall of the cortical bone 20 on the lower half part of the retained physiological femoral head, inputting the designed file in metal 3D printing equipment for printing and forming so as to print the handle body and the porous metal structure on the surface thereof at one time, and then machining the conical connector and the connecting mechanism butted with the lag screw by using the conventional machining cutting process;

Next, selecting a metal bar with an appropriate diameter and machining the lag screw by using the conventional machining cutting process;

Next, designing the three-dimensional model of the fused screw sleeve, designing the necessary location on the surface of the fused screw sleeve into the three-dimensional model of the porous metal structure, and inputting the designed file in the metal 3D printing equipment for direct printing and forming; and Next, obtaining the metal or ceramic femoral head prosthesis by using the currently general metal machining or ceramic sintering and grinding and polishing process in the industry.

Several embodiments of the present invention have been described. Nevertheless, it will be understood that various modifications may be made without departing from the spirit and scope of the invention. Accordingly, other embodiments are within the scope of the following claims.

What is claimed is:

1. A fused femoral stem system, comprising:

a curved handle;

a fixing mechanism; and a femoral head prosthesis;

wherein the fixing mechanism comprises a lag screw and a fused screw sleeve;

wherein the fused screw sleeve is configured to penetrate a large trochanter, and the lag screw is configured to be connected and locked with a connecting mechanism so as to counteract a downward bending moment generated when the femoral head bears the weight load after surgery, and wherein the lag screw is configured to be connected and locked with the connecting mechanism after penetrating through the fused screw sleeve;

wherein one end of the curved handle is provided with a conical connector, the conical connector is cooperatively connected with a conical connecting hole of the femoral head prosthesis, and the other end of the curved handle is inserted from the osteotomy surface of the femoral neck and configured to stretch to the position of a medullary cavity below a small trochanter, and the curved short handle is connected and fixed to the large trochanter through the fixing mechanism;

wherein the fused screw sleeve comprises a hollow tubular body configured to penetrate from the outside of the large trochanter, wherein an outer surface of the hollow tubular body comprises a metal porous structure, and surrounds an inner surface thereof comprising a solid metal sleeve structure, wherein the fused screw sleeve further comprises an annular structure located at the outside of the bone cortex of the large trochanter.

2. The fused femoral stem system according to claim 1, wherein the curved handle comprises a metal handle having a structure that matches a curved surface of an inner wall of a cortical bone on of the femoral head.

3. The fused femoral stem system according to claim 1, wherein the cross section of the curved handle is rectangular, circular, elliptical, drop-shaped or polygonal.

4. The fused femoral stem system according to claim 1, wherein bone fusion layers are arranged at contact positions of the curved handle with the medullary cavity and the large trochanter.

5. The fused femoral stem system according to claim 4, wherein one of the bone fusion layers comprises a rough coating obtained by plasma high-temperature spraying.

6. The fused femoral stem system according to claim 4, wherein one of the bone fusion layers comprise a porous layer formed by sintering metal powder or metal particles or a porous metal layer directly generated by 3D printing.

7. The fused femoral stem system according to claim 1, wherein the connecting mechanism is arranged on a side of the curved handle facing the large trochanter.

8. The fused femoral stem system according to claim 1, wherein the annular structure comprises a porous structure on a side adjacent to a surface of the cortical bone of the large trochanter.

9. The fused femoral stem system according to claim 1, wherein a lower surface of the curved handle comprises a metal porous structure.

* * * * *